United States Patent
Barnes et al.

(10) Patent No.: US 11,337,676 B2
(45) Date of Patent: May 24, 2022

(54) ACOUSTICALLY COMPATIBLE RADIO-FREQUENCY APPLICATOR METHOD AND SYSTEM

(71) Applicant: ENDRA Life Sciences Inc., Ann Arbor, MI (US)

(72) Inventors: Amanda Margaret Barnes, Charlottesville, VA (US); Christopher Nelson Davis, Ann Arbor, MI (US); Michael M. Thornton, London (CA)

(73) Assignee: ENDRA Life Sciences Inc., Ann Arbor, MI (US)

( * ) Notice: Subject to any disclaimer, the term of this patent is extended or adjusted under 35 U.S.C. 154(b) by 372 days.

(21) Appl. No.: 16/714,848

(22) Filed: Feb. 12, 2020

(65) Prior Publication Data

US 2021/0244384 A1 Aug. 12, 2021

(51) Int. Cl.
    *A61B 8/00* (2006.01)
    *G01K 11/22* (2006.01)
    *A61B 5/00* (2006.01)

(52) U.S. Cl.
    CPC .......... *A61B 8/4281* (2013.01); *A61B 5/0093* (2013.01); *A61B 8/4416* (2013.01); *A61B 8/546* (2013.01); *G01K 11/22* (2013.01)

(58) Field of Classification Search
    CPC ... A61B 5/0093; A61B 8/4281; A61B 8/4416; A61B 8/5269; G01K 11/22
    See application file for complete search history.

(56) References Cited

U.S. PATENT DOCUMENTS

| | | |
|---|---|---|
| 2013/0079685 A1 | 3/2013 | Cerwin et al. |
| 2017/0032519 A1 | 2/2017 | Thornton et al. |
| 2017/0351836 A1 | 12/2017 | Thornton et al. |
| 2018/0206826 A1 | 7/2018 | Thornton et al. |
| 2019/0247014 A1 | 8/2019 | Belanger et al. |
| 2020/0264305 A1 | 8/2020 | Brady et al. |

OTHER PUBLICATIONS

Lee Young; PCT International Search Report and Written Opinion; dated Feb. 24, 2021; 8 pages total; WIPO; Alexandria, VA, United States.

*Primary Examiner* — Amelie R Davis
(74) *Attorney, Agent, or Firm* — Stanley E. Jelic

(57) ABSTRACT

A method and system for optimizing RF energy delivery to a tissue ROI with a thermoacoustic system includes directing with a RF applicator, RF energy pulses into the tissue ROI having an object of interest and a reference separated by a boundary; detecting with a thermoacoustic transducer, a multi-polar thermoacoustic signal generated at the boundary in response to the RF energy pulses and processing the multi-polar acoustic signal to determine a peak-to-peak amplitude; detecting with the thermoacoustic transducer, an artifact multi-polar thermoacoustic signal generated at a location other than the boundary and processing it to determine a peak-to-peak amplitude; utilizing an electromagnetic model coupled with a model of patient anatomy to place dielectric or conducting materials near the thermoacoustic transducer or the RF applicator to optimize a signal-to-noise ratio of the multi-polar thermoacoustic signal generated at the boundary or minimize the artifact multi-polar thermoacoustic signal generated at a location other than the boundary; and directing with the RF applicator, RF energy pulses into the ROI for a thermoacoustic measurement and determine a parameter of the object of interest.

20 Claims, 6 Drawing Sheets

ACOUSTICALLY COMPATIBLE RADIO-FREQUENCY APPLICATOR METHOD AND SYSTEM

FIELD

The subject disclosure relates to thermoacoustic imaging and in particular, to an acoustically compatible radio-frequency (RF) applicator (also herein cited as an applicator) method and system.

BACKGROUND

Thermoacoustic imaging is an imaging modality that provides information relating to the thermoelastic properties of tissue. Thermoacoustic imaging uses short pulses of electromagnetic energy, such as radio frequency (RF) pulses, directed into a subject to heat absorbing features within the subject rapidly, which in turn induces acoustic pressure waves that are detected using acoustic receivers, such as one or more thermoacoustic or ultrasound transducer arrays. The detected acoustic pressure waves are analyzed through signal processing and processed for presentation as thermoacoustic images that can be interpreted by an operator.

In order to direct RF pulses into the subject during thermoacoustic imaging, an RF applicator is coupled to tissue adjacent a region of interest (ROI) within the subject to be imaged. Sub-optimal coupling of the RF applicator to the tissue may cause issues such as inefficient energy transfer, reduced heating rates, reduced signal intensity, non-uniform energy deposition, tissue hotspots, tissue overheating, RF power supply damage, and poor image quality. Factors that lead to sub-optimal coupling of the RF applicator to the tissue include variability in the size of the subject, the size of tissue within the subject, the geometry of tissue within the subject, and the composition of tissue within the subject.

SUMMARY

Although conventional techniques for coupling an RF applicator to tissue attempt to resolve these issues, improvements are desired. The embodiments described herein aim to resolve these issues using a method and system for enhancing radio frequency (RF) energy delivery during thermoacoustic imaging.

Accordingly, in one aspect there is provided a thermoacoustic method for optimizing RF energy delivery to a tissue region of interest with a thermoacoustic system, the tissue region of interest comprising an object of interest and at least one reference that are separated by at least one boundary, the method comprising directing, by a RF applicator (also herein cited as a RF applicator), one or more RF energy pulses into the tissue region of interest; detecting, by a thermoacoustic transducer, at least one multi-polar thermoacoustic signal generated at the boundary in response to the one or more RF energy pulses and processing the at least one multi-polar acoustic signal to determine a peak-to-peak amplitude thereof; detecting, by the thermoacoustic transducer, an artifact multi-polar thermoacoustic signal generated at a location other than the boundary in response to the RF energy pulses and processing the artifact multi-polar acoustic signal to determine a peak-to-peak amplitude thereof; applying an electromagnetic model coupled with a model of patient anatomy to determine a placement of the thermoacoustic transducer relative to the RF applicator, wherein the placement optimizes a signal-to-noise ratio of the at least one multi-polar thermoacoustic signal generated at the boundary or minimizes the artifact multi-polar thermoacoustic signal generated at a location other than the boundary; and directing, by the RF applicator, one or more RF energy pulses into the region of interest to make a thermoacoustic measurement and determine a parameter of the object of interest.

In one embodiment, the boundary is at a location between at least two different types of tissue. In another embodiment, the two different types of tissue are selected from a group consisting of muscle and fat; a blood vessel and fat; and liver tissue and kidney tissue.

In one embodiment, a system for enhancing radio frequency energy delivery to a tissue region of interest comprising an object of interest and a reference that are separated by at least one boundary, the system comprises a thermoacoustic imaging system comprising an adjustable radio frequency (RF) applicator configured to emit RF energy pulses into the tissue region of interest and heat tissue therein and a thermoacoustic transducer configured to receive multi-polar thermoacoustic signals generated in response to heating of tissue in the tissue region of interest; and one or more processors configured to process received multi-polar acoustic signals during calibration of the RF applicator to utilize an electromagnetic model coupled with a model of patient anatomy to determine a placement of the thermoacoustic transducer relative to the RF applicator, wherein the placement optimizes a signal-to-noise ratio of the at least one multi-polar thermoacoustic signal generated at the boundary or minimizes the artifact multi-polar thermoacoustic signal generated at a location other than the boundary.

It should be appreciated that this Summary is provided to introduce a selection of concepts in a simplified form that are further described below in the Detailed Description. This Summary is not intended to be used to limit the scope of the claimed subject matter.

BRIEF DESCRIPTION OF THE DRAWINGS

Embodiments will now be described more fully with reference to the accompanying drawings in which.

DETAILED DESCRIPTION OF THE EMBODIMENTS

Figure 1:
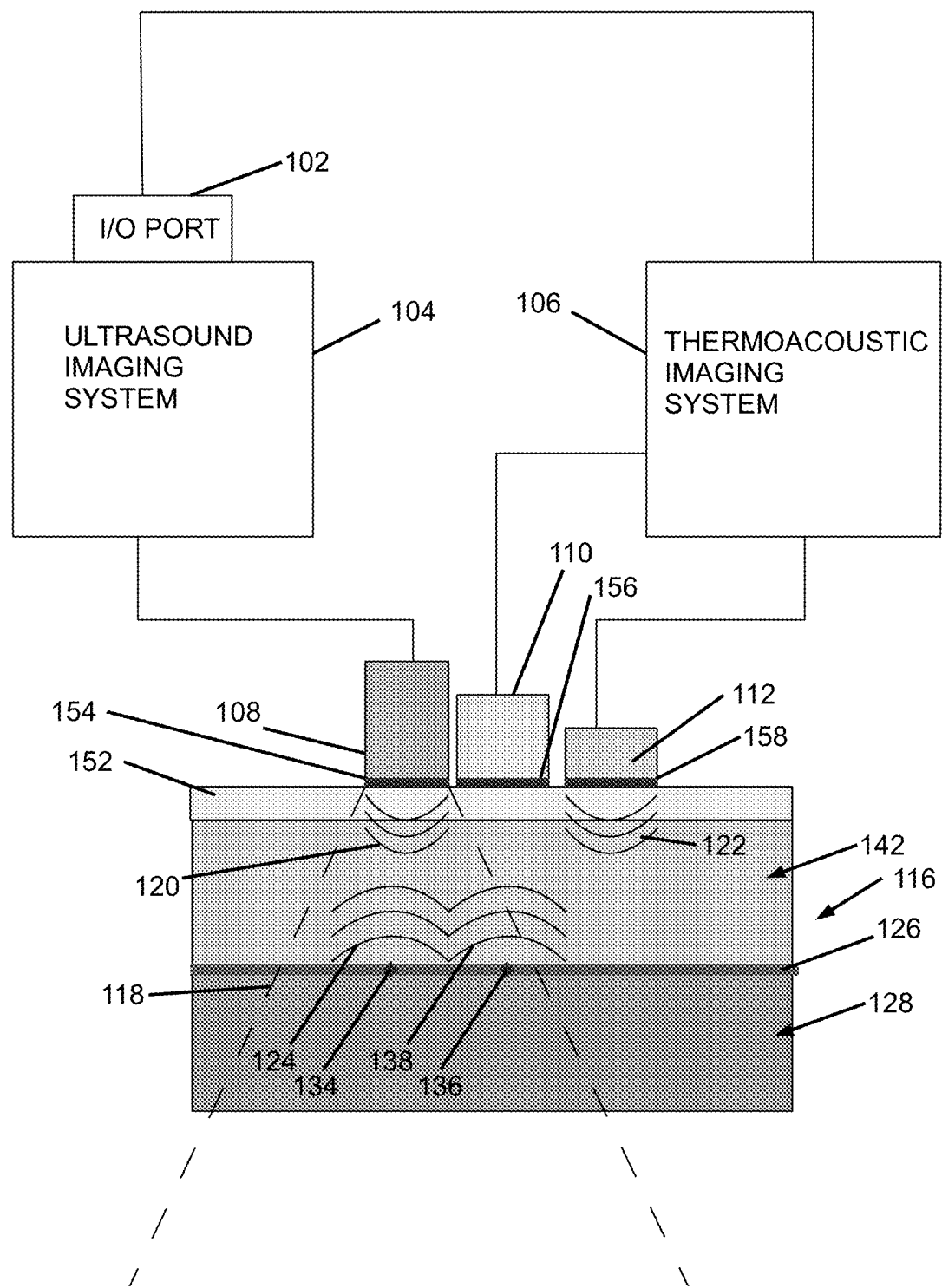
FIG. 1 shows a block diagram of a system, according to an embodiment.

The foregoing summary, as well as the following detailed description of certain examples will be better understood when read in conjunction with the appended drawings. As used herein, an element or feature introduced in the singular and preceded by the word "a" or "an" should be understood as not necessarily excluding the plural of the elements or features. Further, references to "one example" or "one embodiment" are not intended to be interpreted as excluding the existence of additional examples or embodiments that also incorporate the described elements or features. Moreover, unless explicitly stated to the contrary, examples or embodiments "comprising" or "having" or "including" an element or feature or a plurality of elements or features having a particular property may include additional elements or features not having that property. Also, it will be appreciated that the terms "comprises", "has", "includes" means "including but not limited to" and the terms "comprising", "having" and "including" have equivalent meanings.

As used herein, the term "and/or" can include any and all combinations of one or more of the associated listed elements or features.

It will be understood that when an element or feature is referred to as being "on", "attached" to, "connected" to, "coupled" with, "contacting", etc. another element or feature, that element or feature can be directly on, attached to, connected to, coupled with or contacting the other element or feature or intervening elements may also be present. In contrast, when an element or feature is referred to as being, for example, "directly on", "directly attached" to, "directly connected" to, "directly coupled" with or "directly contacting" another element of feature, there are no intervening elements or features present.

It will be understood that spatially relative terms, such as "under", "below", "lower", "over", "above", "upper", "front", "back" and the like, may be used herein for ease of description to describe the relationship of an element or feature to another element or feature as illustrated in the figures. The spatially relative terms can however, encompass different orientations in use or operation in addition to the orientations depicted in the figures.

The embodiments herein describe a method and system for enhancing radio frequency (RF) energy delivery during thermoacoustic imaging. Generally, the method and system utilize an RF applicator to obtain thermoacoustic data of tissue within a region of interest (ROI) of a subject. In one embodiment, the RF applicator has a frequency between about 10 MHz and 100 GHz and has a pulse duration between about 0.1 nanoseconds and 10 microseconds. The thermoacoustic data is analyzed, and then the system is adjusted accordingly.

The method and system are designed to optimize a signal-to-noise ratio of at least one multi-polar thermoacoustic signal generated at the boundary or minimize the artifact multi-polar thermoacoustic signal generated at a location other than the boundary. Additionally, the method and system are designed to minimize RF coupling from RF applicator to the thermoacoustic transducer that can create unwanted thermoacoustic artifacts. Further, the method and system are designed to increase electric field in the tissue for a given RF applicator and power level to improve thermoacoustic signal generation in the ROI.

The system and method can optimize electric field distribution and/or minimize radio frequency interference (RFI) by modifying the RF applicator, modifying the thermoacoustic transducer, modeling patient anatomy, or some combination thereof.

The system and method decrease RF coupling to the thermoacoustic transducer and/or increase electric field coupled to the tissue by adjusting some combination of the following: relative position between the RF applicator and thermoacoustic transducer; placement of dielectric materials in proximity to the thermoacoustic transducer; placement of RF absorbing materials in proximity to the RF applicator; placement of high RF impedance materials in proximity to the RF applicator; and placement of conducting material in proximity to the RF applicator and/or thermoacoustic transducer.

Optimization of the placement, geometry, and electrical properties of the materials is performed using electromagnetic modeling along with a model of patient anatomy. Results of the optimization are used to find configurations in which the electric field is decreased near the thermoacoustic transducer and/or increased in the tissue at the region of interest. Modeling how various designs and manufacturing/assembly steps affect RF coupling and electric field distribution provides insight without building and verifying physical prototypes.

FIG. 1 shows a block diagram of a system embodiment with a peripheral system interfaced to an ultrasound system. Shown are an ultrasound input/output (I/O) port 102, ultrasound imaging system 104, thermoacoustic imaging system 106, ultrasound transducer arrays 108, B-mode image limits 118, thermoacoustic transducer 110, radio-frequency (RF) applicator 112, subject (person) 116, skin and subcutaneous fat layer 152 (both skin and subcutaneous fat shown as one layer), ultrasound waves 120, RF energy pulses 122, intercostal muscle 142, boundary 126, liver 128, boundary locations 134 and 136, and thermoacoustic multipolar signals 124 and 138.

The thermoacoustic imaging system 106 includes a visual display that is integrated with a processor and configured to display an image that is a function of a received ultrasound signal and a received thermoacoustic transducer 110 signal. The thermoacoustic system 106 is configured to receive signals from the ultrasound imaging system 104 and receive signals from the at least one thermoacoustic transducer 110. The thermoacoustic imaging system 106 is configured to resemble one or more of the specified ultrasound imaging system 104 peripheral devices (e.g., USB storage device, printer, monitor) when coupled to the I/O port 102 of the ultrasound imaging system 104 and can display, store, and analyze the data from the ultrasound imaging system 104, where that data is intended for a peripheral device.

The system may also include one or more processors to perform the functionality described herein. In one embodiment, this functionality can be performed by one or more processors of the thermoacoustic imaging system 106. In another embodiment, the one or more processors can be executed in a computer that is communicatively coupled to the thermoacoustic imaging system 106. The one or more processors are configured to execute instructions on a non-transitory computer-readable medium.

In one embodiment, the ultrasound imaging system 104 sends a signal to ultrasound transducer arrays 108, which sends ultrasound waves 120 into subject 116. The ultrasound waves travel through the subject 116 and are reflected to give locations of skin and subcutaneous fat layer 152, intercostal muscle 142, liver 128, boundary 126 between the liver 128 and intercostal muscle 142, and boundary locations 134 and 136. The reflected ultrasound waves are used to generate a B-mode image via the ultrasound imaging system 104 (B-mode image limits 118 shown as dashed line). Next, a user optionally stops imaging with the ultrasound imaging system 104, since position coordinates are now known. The thermoacoustic imaging system 106 sends a signal to the I/O port 102 and mimics a peripheral device that is configured to communicate with the thermoacoustic imaging system 106.

In one embodiment, the thermoacoustic imaging system 106 signal mimics a ISB storage device with I/O event capability and requests image file data from the ultrasound imaging system 104, then storing the image file data.

The thermoacoustic imaging system 106 I/O event is configured to initiate the ultrasound imaging system 104 to (a) transfer an ultrasound image file from the ultrasound imaging system 104 to the thermoacoustic imaging system 106, (b) trigger an event on the thermoacoustic imaging system 106 (e.g., the act of saving and transferring an image from the ultrasound imaging system 104 actually causes the thermoacoustic imaging system 106 to acquire data), or (c) an I/O event on the ultrasound imaging system 104 triggers at least one processing step on the thermoacoustic imaging system 106. Examples of processing steps on the thermoacoustic imaging system 106 are calculating a subject's fat layer thickness, calculating a subject's muscle layer thickness, and calculating a subject's liver fat concentration.

To generate thermoacoustic data, the thermoacoustic imaging system 106 initiates the RF applicator 112 to send RF energy pulses 122 into subject 116. The RF energy 122 pulses are absorbed at different rates in the skin and subcutaneous fat layer 152, intercostal muscle 142, and liver 128. The difference in RF energy absorbed between the intercostal muscle 142 and liver 128 can be measured at the boundary 126. Thermoacoustic multipolar signals 124 and 138 are generated at boundary locations 134 and 136. Thermoacoustic transducer array 110 receives the thermoacoustic multipolar signals 124 and 138 and sends the resulting data to the thermoacoustic imaging system 106, which can calculate a fat concentration in the liver 128 based upon the amplitude and optionally other characteristics of the thermoacoustic multipolar signals 124 and 138.

The ultrasound transducer arrays 108, thermoacoustic transducer 110, and RF applicator 112 all contact the skin and subcutaneous fat layer 152 via an integral matching layer (or lens) for each respective device. FIG. 1 shows ultrasound transducer arrays matching layer 154, thermoacoustic transducer matching layer 156, and RF applicator matching layer 158.

Figure 2:
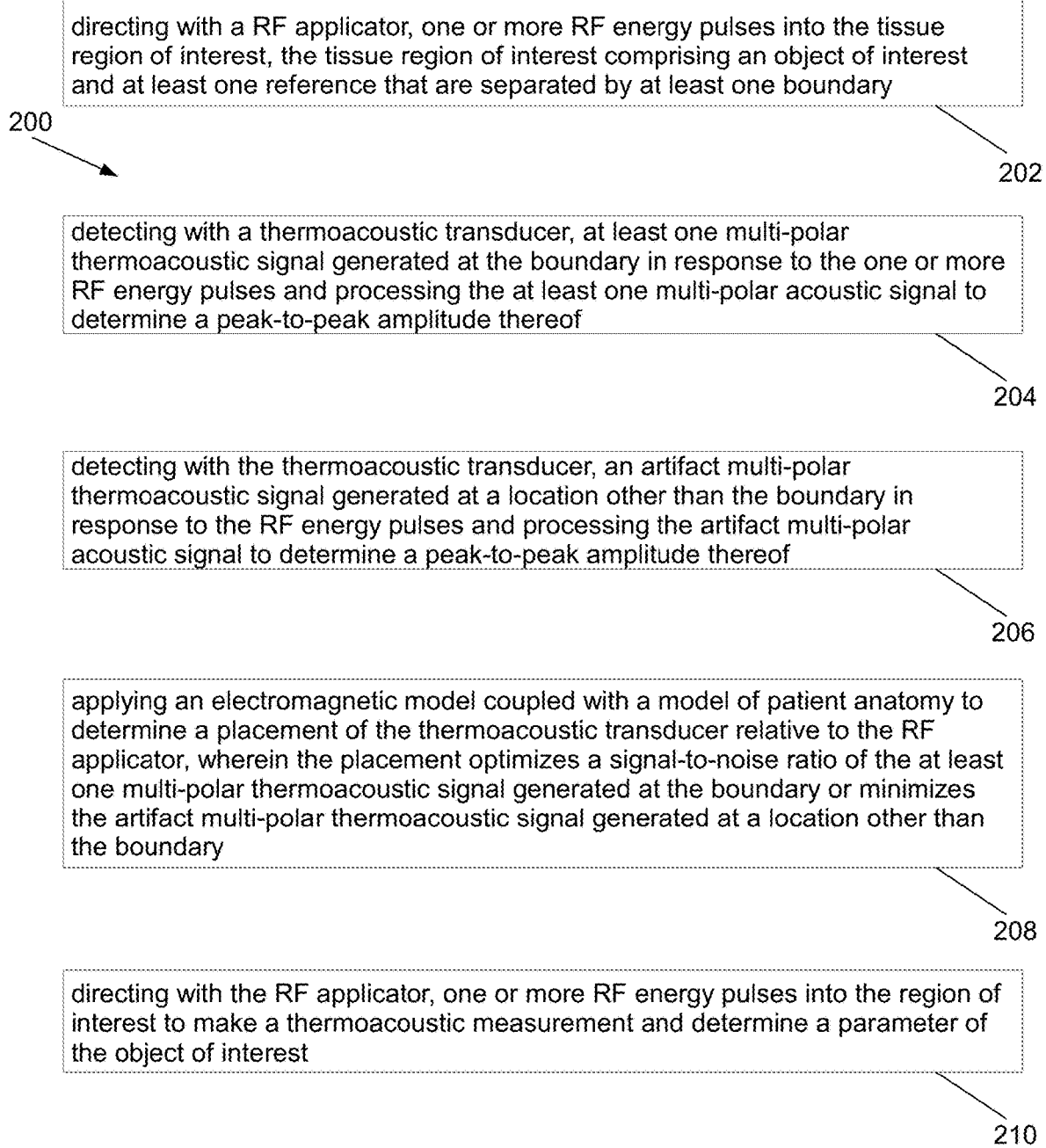
FIG. 2 shows a method, according to an embodiment.

FIG. 2 shows a method 200, according to an embodiment. Method 200 includes the following steps. Step 202 includes directing, with a RF applicator, one or more RF energy pulses into the tissue region of interest, the tissue region of interest comprising an object of interest and at least one reference that are separated by at least one boundary. Step 204 includes detecting, with a thermoacoustic transducer, at least one multi-polar thermoacoustic signal generated at the boundary in response to the one or more RF energy pulses and processing the at least one multi-polar acoustic signal to determine a peak-to-peak amplitude thereof. Step 206 includes detecting with the thermoacoustic transducer, an artifact multi-polar thermoacoustic signal generated at a location other than the boundary in response to the RF energy pulses and processing the artifact multi-polar acoustic signal to determine a peak-to-peak amplitude thereof. This step is done for each region of interest (ROI).

An artifact can occur at any type of interface where two dissimilar tissues or materials are in contact with one another. The dissimilar tissues or materials create a thermoacoustic bipolar signal at the interface. The thermoacoustic signal has a ring down time that depends on the characteristics of the transducer and the strength of the thermoacoustic signal. It is desirable to minimize the thermoacoustic artifact to limit signal interference with the thermoacoustic signal from the region of interest (ROI) that occurs when the thermoacoustic signal from the ROI arrives at the transducer while ring down of the thermoacoustic artifact is still occurring. For example (FIG. 1), a thermoacoustic signal can be generated at the interface between the transducer and the skin. This thermoacoustic signal can propagate into the transducer and overlap in time with the signal that would be generated at the fat and muscle interface, which can be 5 mm or less from the surface of the skin depending on patient anatomy. In another example (FIG. 2), a large thermoacoustic signal is typically generated between the surface of the transmitter element and the skin due the large electric field generated at the aperture of a single element transmitter and the conductivity mismatch between the transmitter and skin. This thermoacoustic signal can reflect off tissue boundaries inside the body, such as a fat-muscle boundary, and, depending on patient anatomy and relative angles between the transducer and transmitter, can overlap in time with signals from the ROI, such as the muscle-liver boundary.

Step 208 includes applying an electromagnetic model coupled with a model of patient anatomy to determine a placement of the thermoacoustic transducer relative to the RF applicator, wherein the placement optimizes a signal-to-noise ratio of the at least one multi-polar thermoacoustic signal generated at the boundary or minimizes the artifact multi-polar thermoacoustic signal generated at a location other than the boundary. Step 208 may be performed for each individual region of interest. The signal noise ratio is optimized by either maximizing the electric field at the boundary and/or minimizing the electric field at locations other than the boundary. In one embodiment, the thermoacoustic imaging system utilizes the electromagnetic model and the model of the patient anatomy to iterate through the various configurations and determine which configuration will provide the optimized settings. The thermoacoustic imaging system can display the optimized configuration for the thermoacoustic transducer and RF applicator as well as any dielectric or conducting materials.

The thermoacoustic transducer and the RF applicator can be positioned in various configurations relative to each other to address imaging issues. Some of these configurations are shown in FIGS. 3 to 9. Although depicted as separate embodiments, it is intended that the system can be configured to include one or more of these configurations.

Figure 3:
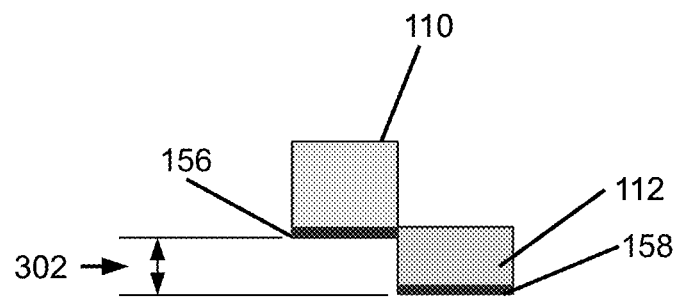
FIG. 3 shows a thermoacoustic transducer recessed relative to an RF applicator, according to an embodiment.

FIG. 3 shows a thermoacoustic transducer recessed relative to an RF applicator, according to an embodiment. Shown are thermoacoustic transducer 110, RF applicator 112, thermoacoustic transducer matching layer 156, RF applicator matching layer 158, and recessed distance gap 302. The thermoacoustic transducer is recessed relative to an RF applicator to reduce RF coupling.

Figure 4:
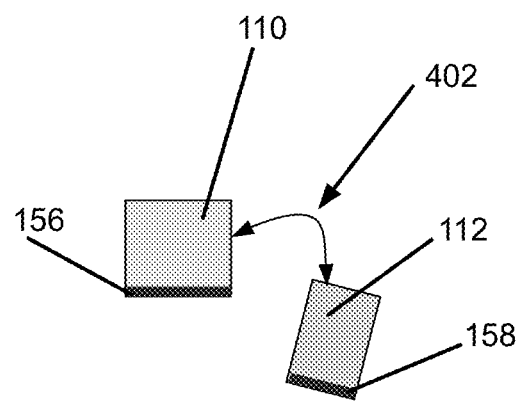
FIG. 4 shows an RF applicator rotated relative to a thermoacoustic transducer, according to an embodiment.

FIG. 4 shows an RF applicator rotated relative to a thermoacoustic transducer, according to an embodiment. Shown are thermoacoustic transducer 110, RF applicator 112, thermoacoustic transducer matching layer 156, RF applicator matching layer 158, and RF applicator rotation angle 402. The RF applicator 112 is rotated relative to the thermoacoustic transducer 110 to increase electric field strength in the ROI.

Figure 5:
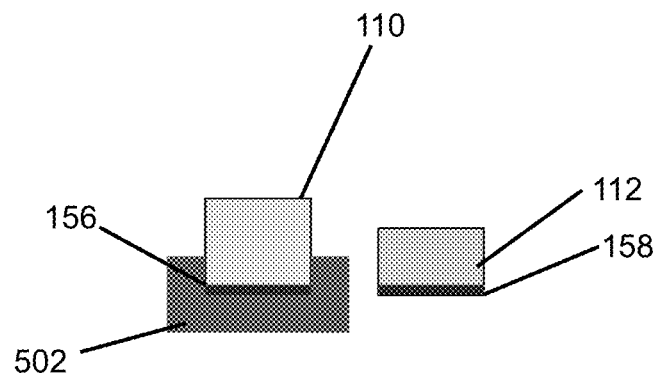
FIG. 5 shows a dielectric material placed around a thermoacoustic transducer, according to an embodiment.

FIG. 5 shows a dielectric material placed around a thermoacoustic transducer, according to an embodiment. Shown are thermoacoustic transducer 110, RF applicator 112, thermoacoustic transducer matching layer 156, RF applicator matching layer 158, and dielectric material 502. Examples of dielectric materials are silicon, ceramic, or the like. The dielectric material reduces RF coupling between the thermoacoustic transducer 110 and the RF applicator 112. Also, there can be an increase in electric field strength in the ROI, because additional RF energy is reflected from the thermoacoustic transducer 110 instead of being absorbed.

Figure 6:
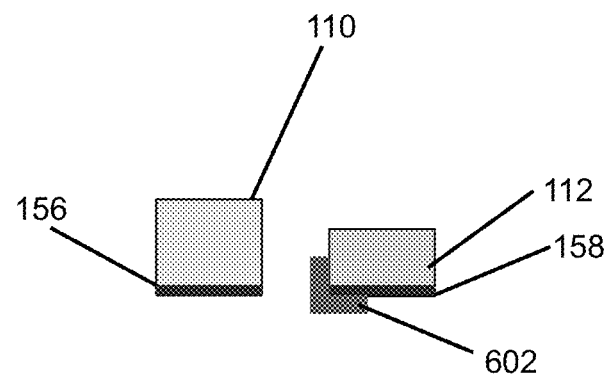
FIG. 6 shows an RF absorbing material placed on a corner of an RF applicator, according to an embodiment.

FIG. 6 shows an RF absorbing material placed on a corner of an RF applicator, according to an embodiment. Shown are thermoacoustic transducer 110, RF applicator 112, thermoacoustic transducer matching layer 156, RF applicator matching layer 158, and RF absorbing material 602. Examples of RF absorbing materials are carbon loaded polymers, foams, or the like. The RF absorbing material 602 reduces RF coupling between the thermoacoustic transducer 110 and the RF applicator 112.

Figure 7:
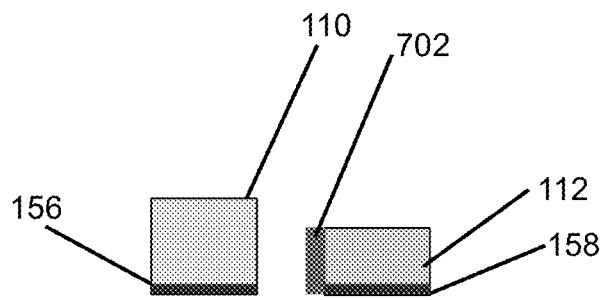
FIG. 7 shows a high RF impedance material placed on an edge of an RF applicator, according to an embodiment.

FIG. 7 shows a high RF impedance material placed on an edge of an RF applicator. Shown are thermoacoustic transducer 110, RF applicator 112, thermoacoustic transducer matching layer 156, RF applicator matching layer 158, and high RF impedance material 702. An example of a high RF impedance material includes nickel filled rubber. The high RF impedance material 702 reduces RF coupling between the thermoacoustic transducer 110 and the RF applicator 112.

Figure 8:
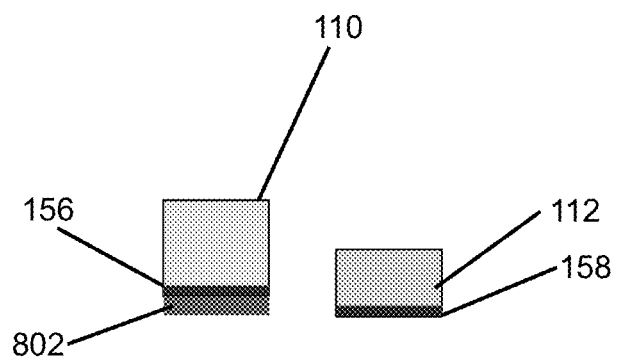
FIG. 8 shows a dielectric material placed on top of a thermoacoustic transducer, according to an embodiment.

FIG. 8 shows a dielectric material placed on top of a thermoacoustic transducer, according to an embodiment. Shown are thermoacoustic transducer 110, RF applicator 112, thermoacoustic transducer matching layer 156, RF applicator matching layer 158, and dielectric material 802. Examples of dielectric material 802 include humimic, gel wax, or the like. The dielectric material 802 reduces RF coupling between the thermoacoustic transducer 110 and the RF applicator 112.

Figure 9:
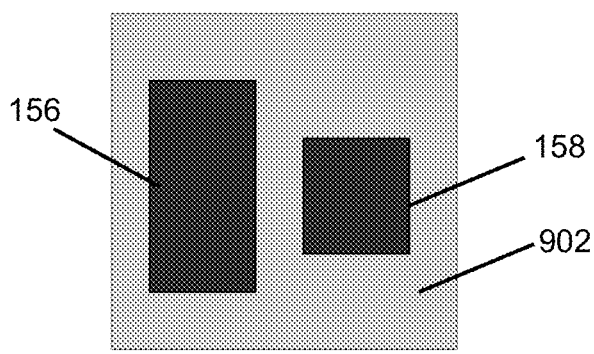
FIG. 9 shows a cross-sectional view with a conducting material placed flush to the surface of the matching layers, according to an embodiment.

FIG. 9 shows a cross-sectional view with a conducting material placed adjacent to the surface of the matching layers. The conducting material does not necessarily have to entirely surround the transducer and RF applicator. Shown are thermoacoustic transducer matching layer 156, RF applicator matching layer 158, and conducting material 902. Examples of conducting material are copper, aluminum, or the like. The conducting material 902 increases in electric field strength in the ROI.

Once the optimized configuration is determined, the thermoacoustic transducer and the RF applicator as well as any dielectric or conducting materials are re-configured to reflect that optimized configuration. In one embodiment, these components can be manually adjusted. In another embodiment, these components are automatically adjusted upon determining the optimized configuration. For example, a motor (not shown) coupled to the thermoacoustic imaging system can rotate an RF applicator relative to the thermoacoustic transducer, as shown in FIG. 4.

Step 210 includes directing, with the RF applicator in the optimized configuration, one or more RF energy pulses into the region of interest to make a thermoacoustic measurement and determine a parameter of the object of interest. Because the system may have implemented a new placement of the thermoacoustic transducer and the RF applicator as well as an application of any new dielectric or conducting materials, the system should have higher quality images than the original configuration.

Although embodiments have been described above with reference to the accompanying drawings, those of skill in the art will appreciate that variations and modifications may be made without departing from the scope thereof as defined by the appended claims.

What is claimed is:

1. A thermoacoustic method for optimizing radio frequency (RF) energy delivery to a tissue region of interest with a thermoacoustic system, the tissue region of interest comprising an object of interest and at least one reference that are separated by a boundary, the method comprising:
   directing, by a RF applicator, one or more RF energy pulses into the tissue region of interest;
   detecting, by a thermoacoustic transducer, at least one multi-polar thermoacoustic signal generated at the boundary in response to the one or more RF energy pulses and processing the at least one multi-polar acoustic signal to determine a peak-to-peak amplitude thereof;
   detecting, by the thermoacoustic transducer, an artifact multi-polar thermoacoustic signal generated at a location other than the boundary in response to the RF energy pulses and processing the artifact multi-polar acoustic signal to determine a peak-to-peak amplitude thereof;
   applying an electromagnetic model coupled with a model of patient anatomy to determine a placement of the thermoacoustic transducer relative to the RF applicator, wherein the placement optimizes a signal-to-noise ratio of the at least one multi-polar thermoacoustic signal generated at the boundary or minimizes the artifact multi-polar thermoacoustic signal generated at a location other than the boundary; and
   directing, by the RF applicator, one or more RF energy pulses into the region of interest to make a thermoacoustic measurement and determine a parameter of the object of interest.

2. The method of claim 1, wherein the boundary is at a location between at least two different types of tissue.

3. The method of claim 2, wherein the two different types of tissue are selected from a group consisting of muscle and fat; a blood vessel and fat; and liver tissue and kidney tissue.

4. The method of claim 1, wherein the placement comprises positioning the thermoacoustic transducer in a recessed position relative to the RF applicator.

5. The method of claim 1, wherein the placement comprises rotating the RF applicator relative to the thermoacoustic transducer.

6. The method of claim 1, wherein the placement comprises positioning a dielectric around the thermoacoustic transducer.

7. The method of claim 1, wherein the placement comprises positioning an RF absorbing material on a corner of the RF applicator.

8. The method of claim 1, wherein the placement comprises positioning an RF impedance material on an edge of the RF applicator.

9. The method of claim 1, wherein the placement comprises positioning a dielectric on top of the thermoacoustic transducer.

10. The method of claim 1, wherein the placement comprises positioning a conducting material adjacent to a surface of a matching layer of the thermoacoustic transducer and a matching layer of the RF applicator.

11. A system for enhancing radio frequency energy delivery to a tissue region of interest comprising an object of interest and a reference that are separated by a boundary, the system comprising:
   a thermoacoustic imaging system comprising an adjustable radio frequency (RF) applicator configured to emit RF energy pulses into the tissue region of interest and heat tissue therein and a thermoacoustic transducer configured to receive multi-polar thermoacoustic signals generated in response to heating of tissue in the tissue region of interest; and one or more processors configured to process received multi-polar acoustic signals during calibration of the RF applicator to utilize an electromagnetic model coupled with a model of patient anatomy to determine a placement of the thermoacoustic transducer relative to the RF applicator, wherein the placement optimizes a signal-to-noise ratio of the at least one multi-polar thermoacoustic signal generated at the boundary or minimizes the artifact multi-polar thermoacoustic signal generated at a location other than the boundary.

12. The system of claim 11, wherein the boundary is at a location between at least two different types of tissue.

13. The system of claim 12, wherein the two different types of tissue are selected from a group consisting of muscle and fat; a blood vessel and fat; and liver tissue and kidney tissue.

14. The system of claim 11, wherein the placement comprises the thermoacoustic transducer in a recessed position relative to the RF applicator.

15. The system of claim 11, wherein the placement comprises the RF applicator rotated relative to the thermoacoustic transducer.

16. The system of claim 11, wherein the placement comprises a dielectric around the thermoacoustic transducer.

17. The system of claim 11, wherein the placement comprises an RF absorbing material on a corner of the RF applicator.

18. The system of claim 11, wherein the placement comprises an RF impedance material on an edge of the RF applicator.

19. The system of claim 11, wherein the placement comprises a dielectric on top of the thermoacoustic transducer.

20. The system of claim 11, wherein the placement comprises a conducting material adjacent to a surface of a matching layer of the thermoacoustic transducer and a matching layer of the RF applicator.

* * * * *